United States Patent
El-Osta (12)

(10) Patent No.: US 9,788,936 B2
(45) Date of Patent: Oct. 17, 2017

(54) CORRECTIVE DEVICE FOR THE POSITIONING OF A FOOT

(71) Applicant: Bassel El-Osta, London (GB)

(72) Inventor: Bassel El-Osta, London (GB)

( * ) Notice: Subject to any disclaimer, the term of this patent is extended or adjusted under 35 U.S.C. 154(b) by 36 days.

(21) Appl. No.: 15/006,183

(22) Filed: Jan. 26, 2016

(65) Prior Publication Data

US 2017/0209255 A1    Jul. 27, 2017

(51) Int. Cl.
*A61F 2/08*    (2006.01)

(52) U.S. Cl.
CPC ....... *A61F 2/0811* (2013.01); *A61F 2002/087* (2013.01); *A61F 2002/0829* (2013.01); *A61F 2002/0888* (2013.01); *A61F 2002/0894* (2013.01)

(58) Field of Classification Search
CPC ......... A61F 2/0811–2002/0888; A61F 2/4202; A61F 5/0113
See application file for complete search history.

(56) References Cited

U.S. PATENT DOCUMENTS

| | | | | |
|---|---|---|---|---|
| 5,382,224 A | * | 1/1995 | Spangler | A61F 5/0113 602/23 |
| 6,171,272 B1 | * | 1/2001 | Akita | A61F 5/0127 602/27 |
| 6,790,165 B2 | * | 9/2004 | Huang | A61F 5/0113 482/79 |

* cited by examiner

*Primary Examiner* — Christopher D Prone

(57) ABSTRACT

A corrective device for the positioning of a foot is an apparatus used to treat foot drop. The apparatus includes a spring, a bone anchor assembly, and a tendon anchor assembly. The spring is used to prevent the foot from drooping downward. The spring includes a coil, a first spring coupler, and a second spring coupler. The first spring coupler is used to connect the coil to the bone anchor assembly. The bone anchor assembly anchors the apparatus to a human tibia. The second spring coupler is used to connect the coil to the tendon anchor assembly. The tendon anchor assembly is used to anchor the apparatus to one or more tendons in the foot. Because the coil is anchored above and below the ankle, rotations about the ankle may be limited by the coil.

19 Claims, 7 Drawing Sheets

CORRECTIVE DEVICE FOR THE POSITIONING OF A FOOT

FIELD OF THE INVENTION

The present invention relates generally to orthopedic devices. More specifically, the present invention is a device which may be surgically connected to a human leg to correct conditions such as foot drop.

BACKGROUND OF THE INVENTION

Foot drop is a significant complication that patients may face as a result of trauma, arthroplastic surgery, a neurophysiological deficit, or even a tumor. Presently, there are various methods to treat foot drop; however, treatment methods can vary depending on what is causing the patient to experience foot drop. Some treatments include surgically repairing or grafting nerves in the foot, physical therapy, and Functional Electrical Stimulation (FES). In addition, ankle-foot orthoses may be used to keep the foot in a single position. Depending on the underlying disorder that causes the patient's foot drop, not all of these treatments may work as desired. Orthoses do not fix the underlying problem, but merely mask it. FES requires that the patient carry an external device at all times. This can be uncomfortable and impractical. Further, physical therapy and nerve repair may not fully treat the patient's underlying disorder.

Accordingly there is a present need for a device capable of correcting foot drop. The present invention is a corrective device that is surgically connected to the leg of a patient. The present invention uses a spring to counteract the weight of the patient's foot, thus reducing or eliminating the dropping of the foot. The present invention is anchored to the tibia of the patient and is sutured through one or more tendons in the foot.

DETAILED DESCRIPTION OF THE INVENTION

All illustrations of the drawings are for the purpose of describing selected versions of the present invention and are not intended to limit the scope of the present invention.

Figure 1:
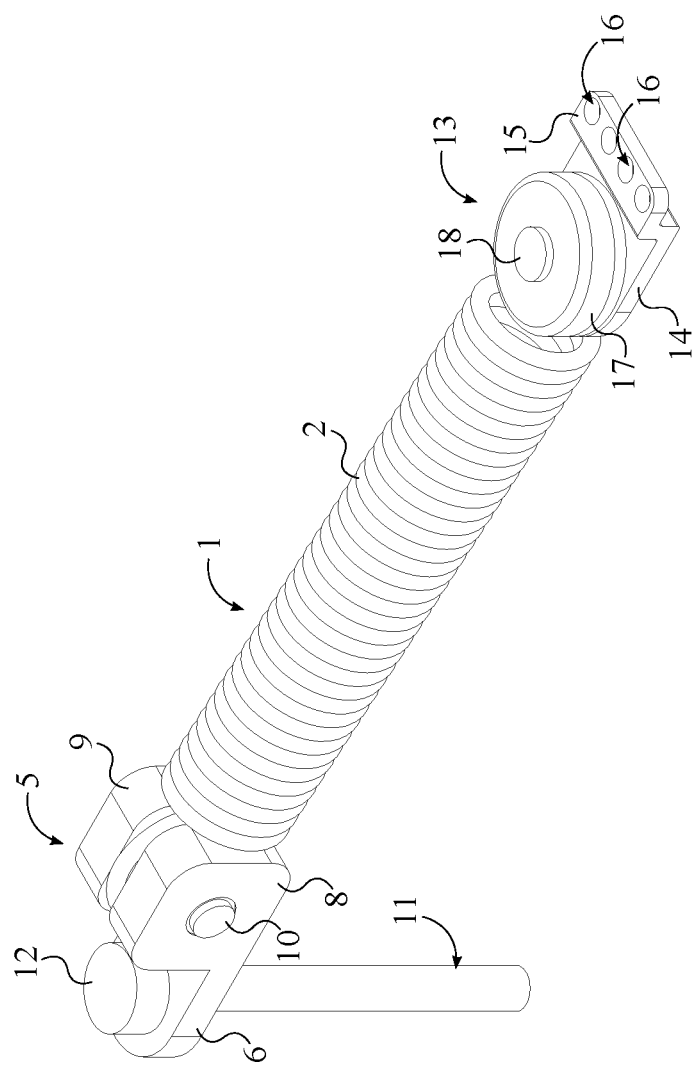
FIG. 1 is a right perspective view of the present invention.
Figure 2:
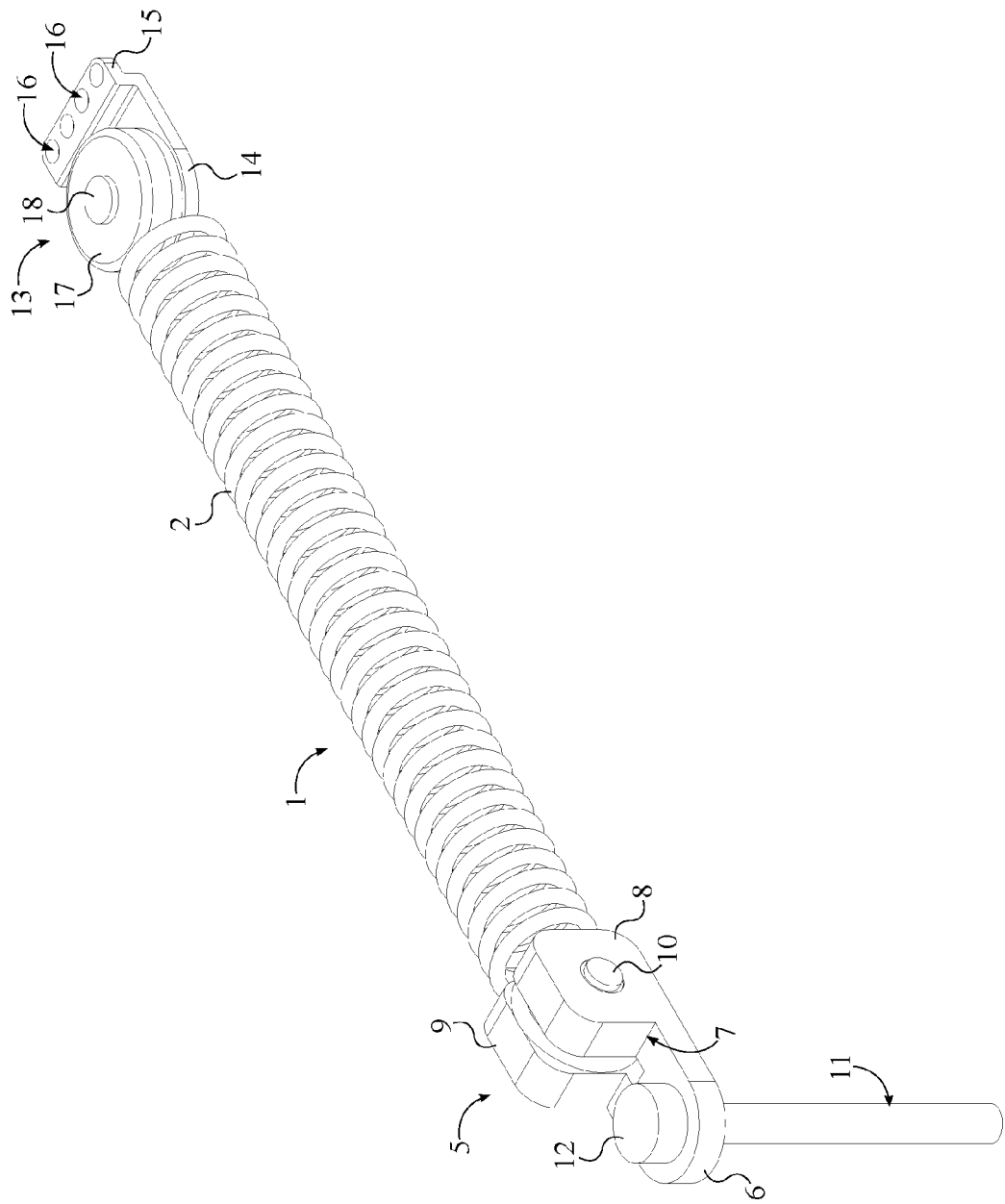
FIG. 2 is a left perspective view of the present invention with the spring in an expanded position.
Figure 3:
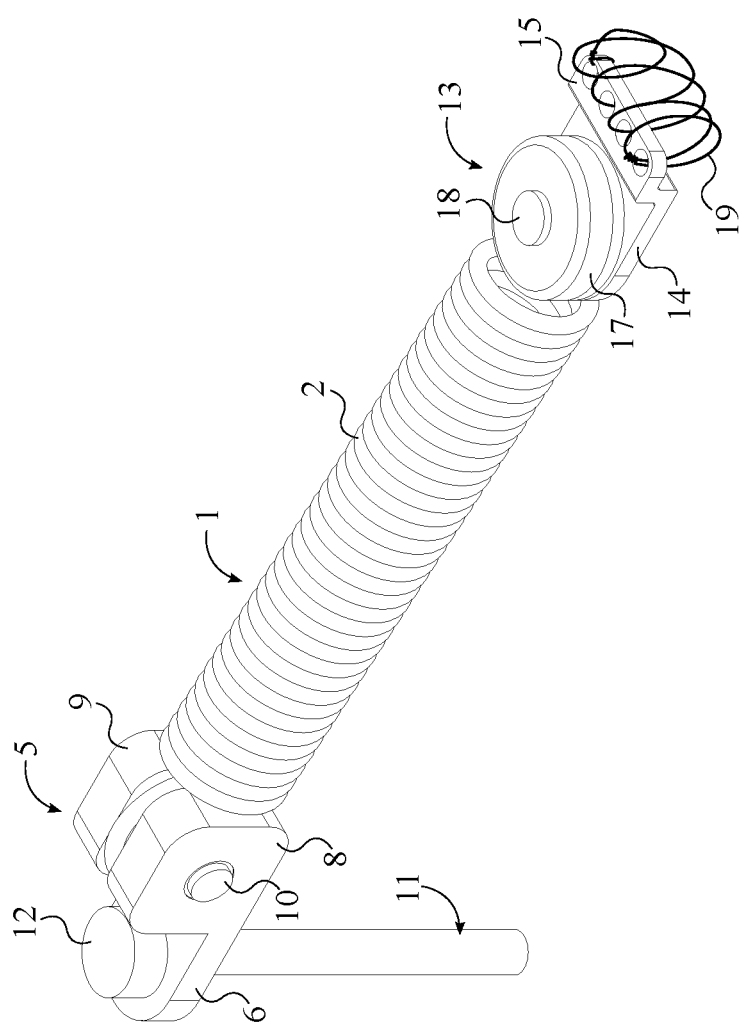
FIG. 3 is a right perspective view of the present invention showing the surgical thread.

With reference to FIGS. 1-3, the present invention is a corrective device for the positioning of a foot. The present invention is used to correctively alter the natural positioning of a human foot such that the foot does not droop at the ankle. This is necessary for those who suffer from foot drop or other similar issues. The present invention comprises a spring 1, a bone anchor assembly 5, and a tendon anchor assembly 13. In the preferred embodiment of the present invention, the spring 1 is a tension spring 1. The spring 1 comprises a coil 2, a first spring coupler 3, and a second spring coupler 4. The coil 2 is used to provide a pulling force which resists the drooping of the foot caused by foot drop. The first spring coupler 3 is connected adjacent to the coil 2, and the second spring coupler 4 is connected adjacent to the coil 2, opposite to the first spring coupler 3. The first spring coupler 3 is used to connect the coil 2 to the bone anchor assembly 5, while the second spring coupler 4 is used to connect the coil 2 to the tendon anchor assembly 13. The first spring coupler 3 and the second spring coupler 4 are positioned perpendicular to each other to accommodate for the mounting method of each assembly. The bone anchor assembly 5 is rotatably mounted to the first spring coupler 3, and the tendon anchor assembly 13 is rotatably mounted to the second spring coupler 4. By connecting the spring 1 to the bone anchor assembly 5 and the tendon anchor assembly 13 through rotatable connections, the spring 1 is able to adjust as the user moves their foot. This is necessary to limit wear on the spring 1 and maximize the level of comfort experienced by the user.

In order to properly select a spring 1 for a particular user, it is necessary to understand the forces experienced by the foot and the ankle during regular use. To investigate such forces, a group of twenty three subjects were tested, using a handheld scale to determine the weight of each subject's foot. A rope and pulley device was used to measure active and passive forces on the foot. Specifically, an aim of the investigation was to determine forces by the Achilles tendon, the extensor digitorum longus, the anterior tibialis, the extensor hallucis longus, and the inferior extensor retinaculum. Such forces from tendons and ligaments were measured both while the foot was in an upward and a downward position. From Table 2a, Table 2b, and Table 3, forces experienced due to the weight of the foot, the inferior extensor retinaculum are shown in active and passive configurations. The active configuration corresponds to a downward positioning of the foot, requiring the activation of the present invention. The passive configuration corresponds an upward positioning of the foot, wherein the present invention is inactive. Table 1a and Table 1b show the calculations for the forces required by the spring 1 in order to successfully lift a human foot. The active and passive forces of the spring 1 are represented by the variable "B" and were calculated using the equations:

$$B_y * T/(\cos(-10)) = (W*D) + (F*L)$$

$$B = B_y/\cos(-10)$$

$$B_x = B*\sin(-10)$$

From the above equations, "W" represents the weight of the foot and "D" represents the distance from the center of rotation for the ankle to the sole of the foot. "F" represents forces perpendicular to the rotation center of rotation and "L" corresponds to the size of the foot. Based on the findings, the positioning of the spring 1 and the strength of the spring 1 may be estimated. In the preferred embodiment of the present invention, the spring 1 is made from stainless steel; however, other medically suitable materials may alternatively be used. One such material may include nitinol.

Figure 6:
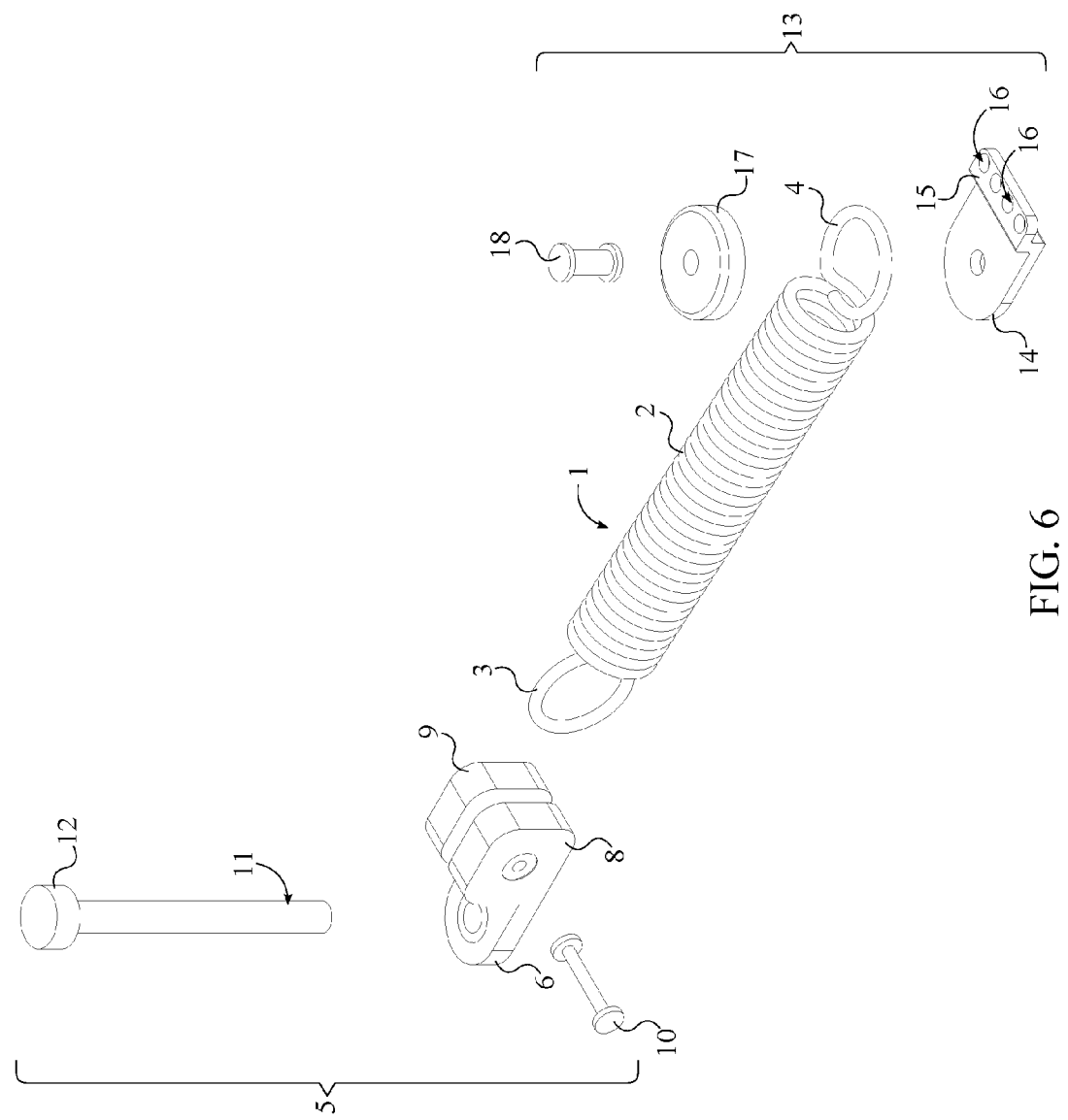
FIG. 6 is an exploded right perspective view of the present invention.

In reference to FIG. 2 and FIG. 6, the bone anchor assembly 5 comprises an anchor plate 6, a first pivot flange 8, a second pivot flange 9, and a pivot pin 10. The anchor plate 6 provides a means of connecting the spring 1 to a human tibia 31. The first pivot flange 8 and the second pivot flange 9 are both connected adjacent to a lateral edge 7 of the anchor plate 6. The first pivot flange 8 and the second pivot flange 9 are positioned opposite to each other along the lateral edge 7. This arrangement creates a gap in between the first pivot flange 8 and the second pivot flange 9. The first spring coupler 3 is positioned in between the first pivot flange 8 and the second pivot flange 9. The fastening pin 5 traverses through the first pivot flange 8, the first spring coupler 3, and the second pivot flange 9. The pivot pin 10 is used to secure the first spring coupler 3 in between the first pivot flange 8 and the second pivot flange 9 and allows the first spring coupler 3 to rotate about the pivot pin 10.

The bone anchor assembly 5 further comprises an anchor bolt 11. The anchor bolt 11 traverses normal and through the anchor plate 6. The anchor bolt 11 engages with a human tibia 31 to secure the bone anchor assembly 5 in place. To prevent the bone anchor assembly 5 from shifting, a head 12 of the anchor bolt 11 is pressed against the anchor plate 6.

In reference to FIG. 3 and FIG. 6, the tendon anchor assembly 13 comprises a base plate 14, an anchor flange 15, a plurality of anchor holes 16, a coupler disk 17, and a coupler pin 18. The anchor flange 15 is connected adjacent to the base plate 14. Each of the plurality of anchor holes 16 traverses normal and through the anchor flange 15. The anchor flange 15 and the plurality of anchor holes 16 provide a means of securing the tendon anchor assembly 13 to a tendon 32 in the human foot. The coupler disk 17 and the base plate 14 are positioned parallel and offset from each other. This arrangement creates a gap in between the coupler disk 17 and the base plate 14 which is large enough for the second spring coupler 4 to fit into. The second spring coupler 4 is positioned in between the base plate 14 and the coupler disk 17. The coupler pin 18 traverses through the anchor plate 6, the second spring coupler 4, and the coupler disk 17.

The coupler pin 18 secures the base plate 14, the second spring coupler 4, and the coupler disk 17 together and allows the second coupler disk 17 to rotate about the coupler pin 18.

Figure 4:
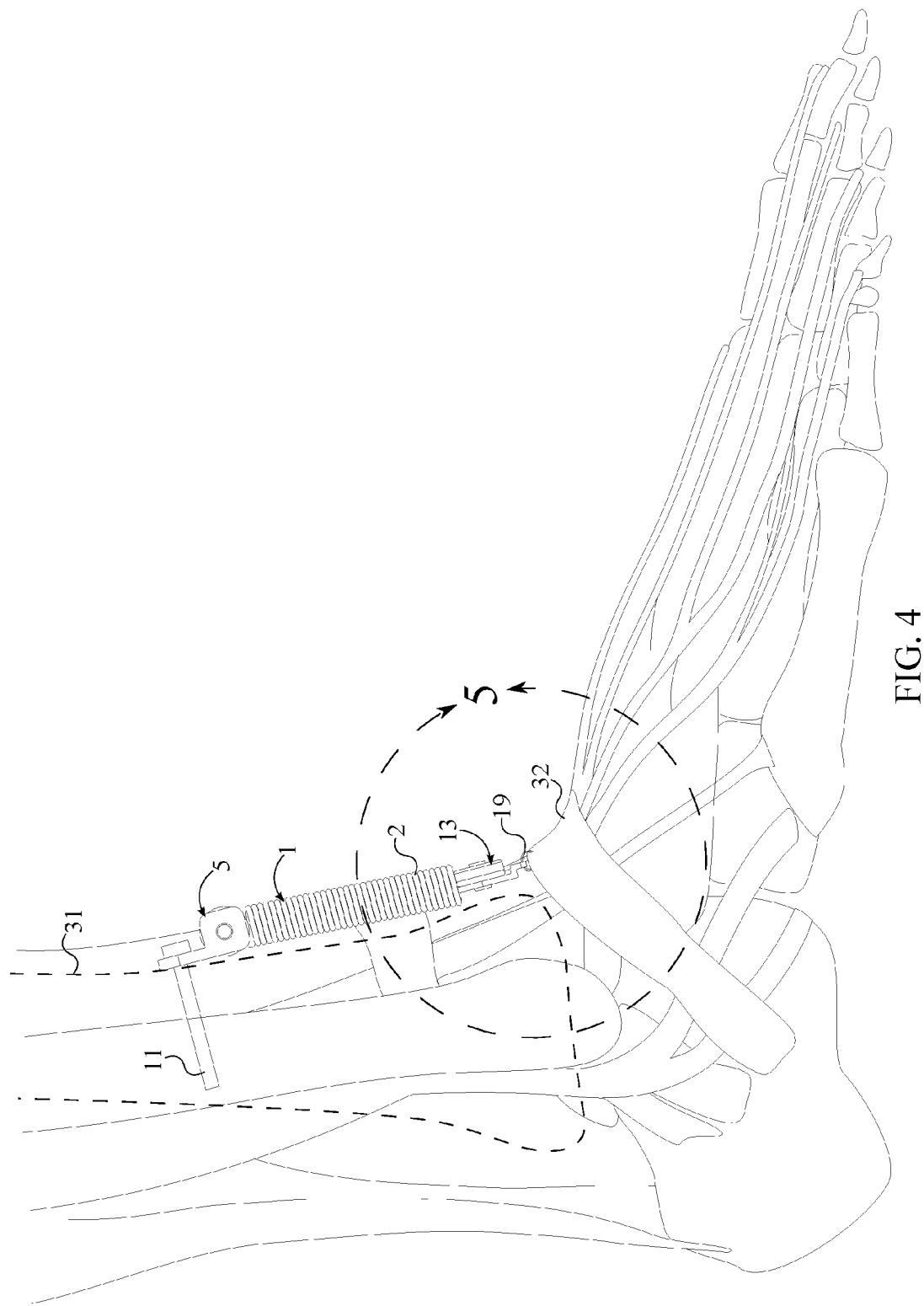
FIG. 4 is a right view of the present invention implanted into a human leg.
Figure 5:
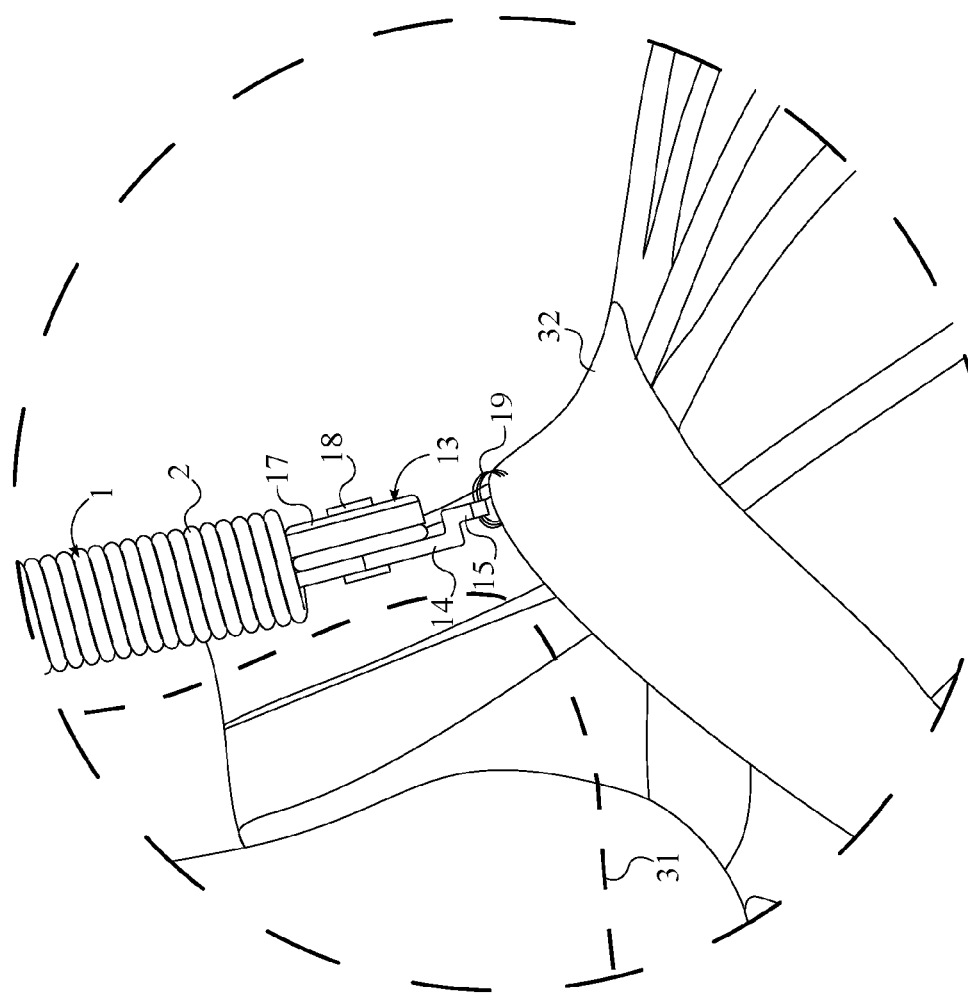
FIG. 5 is a detail view taken from the circle 5 in FIG. 4.

In reference to FIGS. 3-5, the tendon anchor assembly 13 further comprises at least one surgical thread 19. The at least one surgical thread 19 is used to secure the tendon anchor assembly 13 to a tendon 32 in the human foot. To do this, the at least one surgical thread 19 is woven through the plurality of anchor holes 16. To create a strong connection between the anchor flange 15 and the tendon 32, the at least one surgical thread 19 is sutured through the tendon 32. In the preferred embodiment of the present invention, the surgical thread 19 is non-absorbable, braided, and sterile. Moreover, the preferred material of the surgical thread 19 is polyethylene terephthalate; however, other types of materials may alternatively be used.

Figure 7:
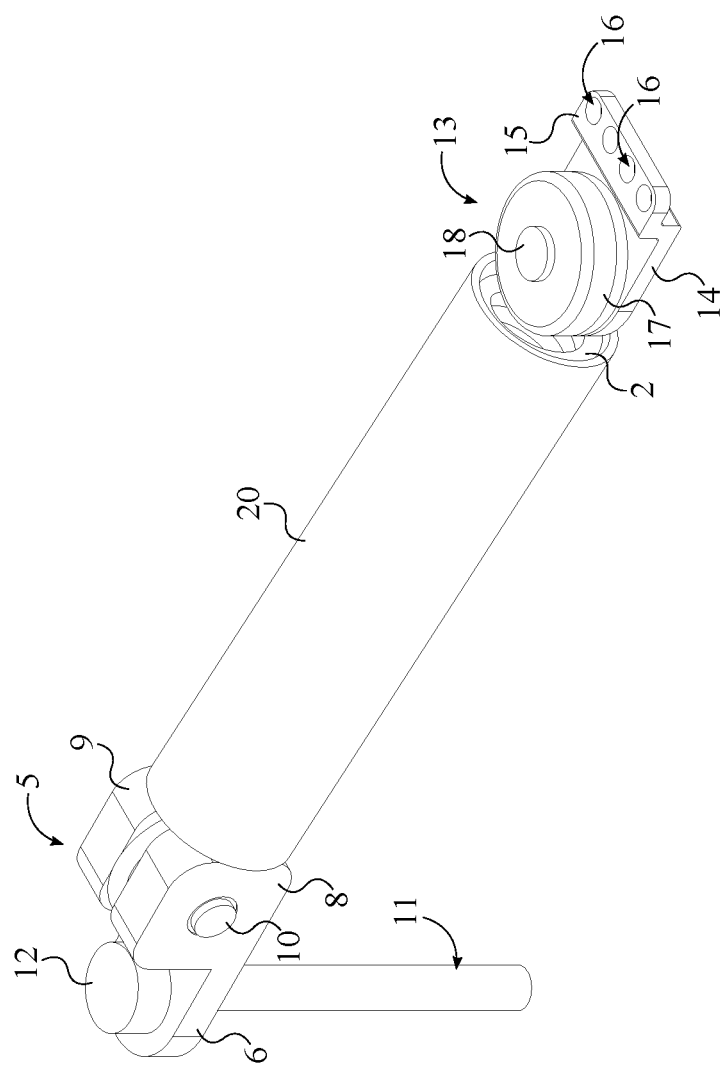
FIG. 7 is a right perspective view of the present invention wherein the spring cover is included.

In reference to FIG. 7, the present invention further comprises a spring cover 20. The spring cover 20 is laterally mounted about the coil 2 and traverses from the first spring coupler 3 to the second spring coupler 4. The spring cover 20 is used to prevent the coil 2 from damaging nearby tissue. As the spring 1 is stretched due to the weight of the foot, gaps are created along the length of the coil 2. As the spring 1 contracts, any tissue that is caught between these gaps may be pinched. The spring cover 20 eliminates the possibility of tissue damage by preventing tissue from contacting the coil 2.

Although the invention has been explained in relation to its preferred embodiment, it is to be understood that many other possible modifications and variations can be made without departing from the spirit and scope of the invention as hereinafter claimed.

TABLE 1a

| Reference Number | Foot Weight (W) (N) | Foot Distance (D) (cm) | Active Force (F) (kg) | Active Force (F) N | Passive Force (F) (kg) | Passive Force (F) (N) | Foot Size (L) EU | Foot Size (L) (cm) | By (Active) (N) | By (Passive) (N) | B (Active) (N) | B (Passive) (N) |
|---|---|---|---|---|---|---|---|---|---|---|---|---|
| 2  | 7.7  | 11.9  | 4 | 39.2 | 1   | 9.8  | 37 | 23.8 | 184 | 47 | 187 | 48 |
| 23 | 7.3  | 12.25 | 4 | 39.2 | 1.5 | 14.7 | 38 | 24.5 | 189 | 72 | 192 | 73 |
| 20 | 8.5  | 11.65 | 4 | 39.2 | 1.8 | 17.6 | 36 | 23.3 | 278 | 81 | 283 | 82 |
| 13 | 8.5  | 11.9  | 3 | 29.4 | 2   | 19.8 | 37 | 23.8 | 367 | 93 | 373 | 95 |
| 10 | 8    | 11.9  | 8 | 78.4 | 2   | 19.8 | 37 | 23.8 | 367 | 93 | 373 | 95 |
| 8  | 9.3  | 11.9  | 4 | 39.2 | 2   | 19.8 | 37 | 23.8 | 184 | 94 | 187 | 96 |
| 18 | 7.4  | 12.25 | 4 | 39.2 | 2   | 19.8 | 38 | 24.5 | 189 | 96 | 192 | 98 |
| 14 | 9.6  | 12.55 | 6 | 58.8 | 2   | 19.8 | 39 | 25.1 | 291 | 99 | 296 | 101 |
| 15 | 9.3  | 12.55 | 4 | 39.2 | 2   | 19.8 | 39 | 25.1 | 194 | 99 | 197 | 101 |
| 16 | 13.5 | 12.55 | 4 | 39.2 | 2   | 19.8 | 39 | 25.1 | 195 | 99 | 198 | 101 |
| 17 | 9    | 12.7  | 4 | 39.2 | 2   | 19.8 | 40 | 25.4 | 196 | 99 | 199 | 101 |
| 4  | 13.7 | 12.55 | 6 | 58.8 | 2   | 19.8 | 39 | 25.1 | 291 | 99 | 296 | 101 |

TABLE 1b

| Reference Number | Foot Weight (W) (N) | Foot Distance (D) (cm) | Active Force (F) (kg) | Active Force (F) N | Passive Force (F) (kg) | Passive Force (F) (N) | Foot Size (L) EU | Foot Size (L) (cm) | By (Active) (N) | By (Passive) (N) | B (Active) (N) | B (Passive) (N) |
|---|---|---|---|---|---|---|---|---|---|---|---|---|
| 3  | 8.9  | 12.7  | 5 | 49   | 2 | 19.8 | 40 | 25.4 | 184 | 100 | 187 | 102 |
| 19 | 8.6  | 12.85 | 4 | 39.2 | 2 | 19.8 | 41 | 25.7 | 199 | 101 | 202 | 103 |
| 24 | 10.5 | 13.35 | 4 | 39.2 | 2 | 19.8 | 43 | 26.7 | 207 | 110 | 210 | 112 |
| 21 | 10.7 | 14.3  | 6 | 58.8 | 2 | 19.8 | 46 | 28.6 | 331 | 113 | 336 | 115 |
| 12 | 13   | 14.3  | 8 | 78.4 | 2 | 19.8 | 46 | 28.6 | 442 | 113 | 449 | 115 |
| 22 | 13.5 | 13.35 | 4 | 39.2 | 3 | 29.4 | 43 | 26.7 | 207 | 156 | 210 | 159 |
| 11 | 6.9  | 11.75 | 6 | 58.8 | 4 | 39.2 | 36 | 23.5 | 272 | 181 | 276 | 184 |
| 9  | 11.4 | 12.7  | 8 | 78.4 | 4 | 39.2 | 40 | 25.4 | 392 | 197 | 398 | 200 |
| 7  | 9.9  | 13    | 6 | 58.8 | 4 | 39.2 | 42 | 26   | 301 | 197 | 306 | 200 |
| 6  | 12   | 13.95 | 9 | 88.2 | 4 | 39.2 | 45 | 27.9 | 483 | 202 | 491 | 205 |

TABLE 1b-continued

| Reference Number | Foot Weight (W) (N) | Foot Distance (D) (cm) | Active Force (F) (kg) | (N) | Passive Force (F) (kg) | (N) | Foot Size (L) EU | (cm) | By (Active) (N) | By (Passive) (N) | B (Active) (N) | B (Passive) (N) |
|---|---|---|---|---|---|---|---|---|---|---|---|---|
| 5 | 11.3 | 13.95 | 6 | 58.8 | 4 | 39.2 | 45 | 27.9 | 323 | 216 | 328 | 220 |
| 1 | 15.64 | 13.95 | 10 | 98 | 4 | 39.2 | 45 | 27.9 | 538 | 217 | 547 | 221 |

TABLE 2a

| Reference Number | Foot Weight (W) (N) | Foot Distance (D) (cm) | Active Force (F) (kg) | (N) | Passive Force (F) (kg) | (N) | Y Force (Active) (N) | Y Force (Passive) (N) | X Force (Active) (N) | X Force (Passive) (N) |
|---|---|---|---|---|---|---|---|---|---|---|
| 2 | 7.7 | 11.9 | 4 | 39.2 | 1 | 9.8 | 107 | 27 | 114 | 24.5 |
| 23 | 7.3 | 12.25 | 4 | 39.2 | 1.5 | 14.7 | 107 | 40.5 | 114 | 43.1 |
| 20 | 8.5 | 11.65 | 4 | 39.2 | 1.8 | 17.6 | 107 | 49 | 114 | 52.2 |
| 13 | 8.5 | 11.9 | 3 | 29.4 | 2 | 19.8 | 81 | 54.5 | 86.2 | 58 |
| 10 | 8 | 11.9 | 8 | 78.4 | 2 | 19.8 | 215 | 54.5 | 229 | 58 |
| 8 | 9.3 | 11.9 | 4 | 39.2 | 2 | 19.8 | 107 | 54.5 | 114 | 58 |
| 18 | 7.4 | 12.25 | 4 | 39.2 | 2 | 19.8 | 107 | 54.5 | 114 | 58 |
| 14 | 9.6 | 12.55 | 6 | 58.8 | 2 | 19.8 | 162 | 54.5 | 173 | 58 |
| 15 | 9.3 | 12.55 | 4 | 39.2 | 2 | 19.8 | 107 | 54.5 | 114 | 58 |
| 16 | 13.5 | 12.55 | 4 | 39.2 | 2 | 19.8 | 107 | 54.5 | 114 | 58 |
| 17 | 9 | 12.7 | 4 | 39.2 | 2 | 19.8 | 107 | 54.5 | 114 | 58 |
| 4 | 13.7 | 12.55 | 6 | 58.8 | 2 | 19.8 | 162 | 54.5 | 173 | 58 |

TABLE 2b

| Reference Number | Foot Weight (W) (N) | Foot Distance (D) (cm) | Active Force (F) (kg) | (N) | Passive Force (F) (kg) | (N) | Y Force (Active) (N) | Y Force (Passive) (N) | X Force (Active) (N) | X Force (Passive) (N) |
|---|---|---|---|---|---|---|---|---|---|---|
| 3 | 8.9 | 12.7 | 5 | 49 | 2 | 19.8 | 134 | 54.5 | 143 | 58 |
| 19 | 8.6 | 12.85 | 4 | 39.2 | 2 | 19.8 | 107 | 54.5 | 114 | 58 |
| 24 | 10.5 | 13.35 | 4 | 39.2 | 2 | 19.8 | 107 | 54.5 | 114 | 58 |
| 21 | 10.7 | 14.3 | 6 | 58.8 | 2 | 19.8 | 162 | 54.5 | 173 | 58 |
| 12 | 13 | 14.3 | 8 | 78.4 | 2 | 19.8 | 215 | 54.5 | 229 | 58 |
| 22 | 13.5 | 13.35 | 4 | 39.2 | 3 | 29.4 | 107 | 81 | 114 | 86.2 |
| 11 | 6.9 | 11.75 | 6 | 58.8 | 4 | 39.2 | 162 | 107 | 172.4 | 114 |
| 9 | 11.4 | 12.7 | 8 | 78.4 | 4 | 39.2 | 215 | 107 | 229 | 114 |
| 7 | 9.9 | 13 | 6 | 58.8 | 4 | 39.2 | 162 | 107 | 172.4 | 114 |
| 6 | 12 | 13.95 | 9 | 88.2 | 4 | 39.2 | 245 | 107 | 261 | 114 |
| 5 | 11.3 | 13.95 | 6 | 58.8 | 4 | 39.2 | 162 | 107 | 172.4 | 114 |
| 1 | 15.64 | 13.95 | 10 | 98 | 4 | 39.2 | 270 | 107 | 287 | 114 |

TABLE 3

| Reference Number | Foot Weight (W) (N) | Foot Distance (D) (cm) | Active Force (F) (kg) | (N) | Passive Force (F) (kg) | (N) | Q Force (Active) (N) | Q Force (Passive) (N) |
|---|---|---|---|---|---|---|---|---|
| 2 | 7.7 | 11.9 | 4 | 39.2 | 1 | 9.8 | 37 | 9.2 |
| 23 | 7.3 | 12.25 | 4 | 39.2 | 1.5 | 14.7 | 37 | 14 |
| 20 | 8.5 | 11.65 | 4 | 39.2 | 1.8 | 17.6 | 37 | 16.5 |
| 13 | 8.5 | 11.9 | 3 | 29.4 | 2 | 19.8 | 28 | 18.6 |
| 10 | 8 | 11.9 | 8 | 78.4 | 2 | 19.8 | 74 | 18.6 |
| 8 | 9.3 | 11.9 | 4 | 39.2 | 2 | 19.8 | 37 | 18.6 |
| 18 | 7.4 | 12.25 | 4 | 39.2 | 2 | 19.8 | 37 | 18.6 |
| 14 | 9.6 | 12.55 | 6 | 58.8 | 2 | 19.8 | 55 | 18.6 |
| 15 | 9.3 | 12.55 | 4 | 39.2 | 2 | 19.8 | 37 | 18.6 |
| 16 | 13.5 | 12.55 | 4 | 39.2 | 2 | 19.8 | 37 | 18.6 |
| 17 | 9 | 12.7 | 4 | 39.2 | 2 | 19.8 | 37 | 18.6 |

TABLE 3-continued

| Reference Number | Foot Weight (W) (N) | Foot Distance (D) (cm) | Active Force (F) (kg) | Active Force (F) (N) | Passive Force (F) (kg) | Passive Force (F) (N) | Q Force (Active) (N) | Q Force (Passive) (N) |
|---|---|---|---|---|---|---|---|---|
| 4 | 13.7 | 12.55 | 6 | 58.8 | 2 | 19.8 | 55 | 18.6 |
| 3 | 8.9 | 12.7 | 5 | 49 | 2 | 19.8 | 46 | 18.6 |
| 19 | 8.6 | 12.85 | 4 | 39.2 | 2 | 19.8 | 37 | 18.6 |
| 24 | 10.5 | 13.35 | 4 | 39.2 | 2 | 19.8 | 37 | 18.6 |
| 21 | 10.7 | 14.3 | 6 | 58.8 | 2 | 19.8 | 55 | 18.6 |
| 12 | 13 | 14.3 | 8 | 78.4 | 2 | 19.8 | 74 | 18.6 |
| 22 | 13.5 | 13.35 | 4 | 39.2 | 3 | 29.4 | 37 | 28 |
| 11 | 6.9 | 11.75 | 6 | 58.8 | 4 | 39.2 | 55 | 37 |
| 9 | 11.4 | 12.7 | 8 | 78.4 | 4 | 39.2 | 74 | 37 |
| 7 | 9.9 | 13 | 6 | 58.8 | 4 | 39.2 | 55 | 37 |
| 6 | 12 | 13.95 | 9 | 88.2 | 4 | 39.2 | 83 | 37 |
| 5 | 11.3 | 13.95 | 6 | 58.8 | 4 | 39.2 | 55 | 37 |
| 1 | 15.64 | 13.95 | 10 | 98 | 4 | 39.2 | 92 | 37 |

What is claimed is:

1. A corrective device for the positioning of a foot comprises:
   a spring;
   a bone anchor assembly;
   a tendon anchor assembly;
   the spring comprises a coil, a first spring coupler, and a second spring coupler;
   the first spring coupler being connected adjacent to the coil;
   the second spring coupler being connected adjacent to the coil, opposite to the first spring coupler;
   the first spring coupler and the second spring coupler being positioned perpendicular to each other;
   the bone anchor assembly being rotatably mounted to the first spring coupler; and
   the tendon anchor assembly being rotatably mounted to the second spring coupler.

2. The corrective device for the positioning of a foot as claimed in claim 1 comprises:
   the bone anchor assembly comprises an anchor plate, a first pivot flange, a second pivot flange, and a pivot pin;
   the first pivot flange being connected adjacent to a lateral edge of the anchor plate;
   the second pivot flange being connected adjacent to the lateral edge of the anchor plate;
   the first pivot flange and the second pivot flange being positioned opposite to each other along the lateral edge;
   the first spring coupler being positioned in between the first pivot flange and the second pivot flange; and
   the pivot pin traversing through the first pivot flange, the first spring coupler, and the second pivot flange.

3. The corrective device for the positioning of a foot as claimed in claim 2 comprises:
   the bone anchor assembly further comprises an anchor bolt;
   the anchor bolt traversing normal and through the anchor plate, wherein the anchor bolt is configured to be engaged with a human tibia; and
   a head of the anchor bolt being pressed against the anchor plate.

4. The corrective device for the positioning of a foot as claimed in claim 1 comprises:
   the tendon anchor assembly comprises a base plate, an anchor flange, a plurality of anchor holes, a coupler disk, and a coupler pin;
   the anchor flange being connected adjacent to the base plate;
   each of the plurality of anchor holes traversing normal and through the anchor flange;
   the coupler disk and the base plate being positioned parallel and offset from each other;
   the second spring coupler being positioned in between the base plate and the coupler disk; and
   the coupler pin traversing through the anchor plate, the second spring coupler, and the coupler disk.

5. The corrective device for the positioning of a foot as claimed in claim 4 comprises:
   the tendon anchor assembly further comprises at least one surgical thread; and
   the at least one surgical thread being woven through the plurality of anchor holes, wherein the at least one surgical thread is configured to be sutured through a tendon.

6. The corrective device for the positioning of a foot as claimed in claim 1 comprises:
   a spring cover;
   the spring cover surrounding the coil; and
   the spring cover traversing from the first spring coupler to the second spring coupler.

7. The corrective device for the positioning of a foot as claimed in claim 1, wherein the spring is a tension spring.

8. A corrective device for the positioning of a foot comprises:
   a spring;
   a bone anchor assembly;
   a tendon anchor assembly;
   the spring comprises a coil, a first spring coupler, and a second spring coupler;
   the first spring coupler being connected adjacent to the coil;
   the second spring coupler being connected adjacent to the coil, opposite to the first spring coupler;
   the first spring coupler and the second spring coupler being positioned perpendicular to each other;
   the bone anchor assembly being rotatably mounted to the first spring coupler;
   the tendon anchor assembly being rotatably mounted to the second spring coupler;
   the bone anchor assembly comprises an anchor plate, a first pivot flange, a second pivot flange, and a pivot pin;
   the first pivot flange being connected adjacent to a lateral edge of the anchor plate;
   the second pivot flange being connected adjacent to the lateral edge of the anchor plate;

the first pivot flange and the second pivot flange being positioned opposite to each other along the lateral edge;

the first spring coupler being positioned in between the first pivot flange and the second pivot flange; and the fastening pin traversing through the first pivot flange, the first spring coupler, and the second pivot flange.

9. The corrective device for the positioning of a foot as claimed in claim 8 comprises:

the bone anchor assembly further comprises an anchor bolt;

the anchor bolt traversing normal and through the anchor plate, wherein the anchor bolt is configured to be engaged with a human tibia; and a head of the anchor bolt being pressed against the anchor plate.

10. The corrective device for the positioning of a foot as claimed in claim 8 comprises:

the tendon anchor assembly comprises a base plate, an anchor flange, a plurality of anchor holes, a coupler disk, and a coupler pin;

the anchor flange being connected adjacent to the base plate;

each of the plurality of anchor holes traversing normal and through the anchor flange;

the coupler disk and the base plate being positioned parallel and offset from each other;

the second spring coupler being positioned in between the base plate and the coupler disk; and the coupler pin traversing through the anchor plate, the second spring coupler, and the coupler disk.

11. The corrective device for the positioning of a foot as claimed in claim 10 comprises:

the tendon anchor assembly further comprises at least one surgical thread; and the at least one surgical thread being woven through the plurality of anchor holes, wherein the at least one surgical thread is configured to be sutured through a tendon.

12. The corrective device for the positioning of a foot as claimed in claim 8 comprises:

a spring cover;

the spring cover surrounding the coil; and the spring cover traversing from the first spring coupler to the second spring coupler.

13. The corrective device for the positioning of a foot as claimed in claim 8, wherein the spring is a tension spring.

14. A corrective device for the positioning of a foot comprises:

a spring;

a bone anchor assembly;

a tendon anchor assembly;

the spring comprises a coil, a first spring coupler, and a second spring coupler;

the first spring coupler being connected adjacent to the coil;

the second spring coupler being connected adjacent to the coil, opposite to the first spring coupler;

the first spring coupler and the second spring coupler being positioned perpendicular to each other;

the bone anchor assembly being rotatably mounted to the first spring coupler;

the tendon anchor assembly being rotatably mounted to the second spring coupler;

the tendon anchor assembly comprises a base plate, an anchor flange, a plurality of anchor holes, a coupler disk, and a coupler pin;

the anchor flange being connected adjacent to the base plate;

each of the plurality of anchor holes traversing normal and through the anchor flange;

the coupler disk and the base plate being positioned parallel and offset from each other;

the second spring coupler being positioned in between the base plate and the coupler disk; and the coupler pin traversing through the anchor plate, the second spring coupler, and the coupler disk.

15. The corrective device for the positioning of a foot as claimed in claim 14 comprises:

the bone anchor assembly comprises an anchor plate, a first pivot flange, a second pivot flange, and a pivot pin;

the first pivot flange being connected adjacent to a lateral edge of the anchor plate;

the second pivot flange being connected adjacent to the lateral edge of the anchor plate;

the first pivot flange and the second pivot flange being positioned opposite to each other along the lateral edge;

the first spring coupler being positioned in between the first pivot flange and the second pivot flange; and the fastening pin traversing through the first pivot flange, the first spring coupler, and the second pivot flange.

16. The corrective device for the positioning of a foot as claimed in claim 15 comprises:

the bone anchor assembly further comprises an anchor bolt;

the anchor bolt traversing normal and through the anchor plate, wherein the anchor bolt is configured to be engaged with a human tibia; and a head of the anchor bolt being pressed against the anchor plate.

17. The corrective device for the positioning of a foot as claimed in claim 14 comprises:

the tendon anchor assembly further comprises at least one surgical thread; and the at least one surgical thread being woven through the plurality of anchor holes, wherein the at least one surgical thread is configured to be sutured through a tendon.

18. The corrective device for the positioning of a foot as claimed in claim 14 comprises:

a spring cover;

the spring cover surrounding the coil; and the spring cover traversing from the first spring coupler to the second spring coupler.

19. The corrective device for the positioning of a foot as claimed in claim 14, wherein the spring is a tension spring.

* * * * *